United States Patent
Ciccone et al.

(10) Patent No.: US 10,583,281 B2
(45) Date of Patent: *Mar. 10, 2020

(54) CATCH ASSEMBLY FOR RELEASABLY CONNECTING FLUID CONDUITS

(71) Applicant: WilMarc Holdings, LLC, Fort Collins, CO (US)

(72) Inventors: Paul C. Ciccone, Wellington, CO (US); William A. Coulson, Fort Collins, CO (US); Marcia Coulson, Fort Collins, CO (US)

(73) Assignee: WilMarc Holdings, LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/503,757

(22) Filed: Jul. 5, 2019

(65) Prior Publication Data

US 2019/0329017 A1     Oct. 31, 2019

Related U.S. Application Data

(63) Continuation of application No. 15/912,280, filed on Mar. 5, 2018, now Pat. No. 10,350,401.

(Continued)

(51) Int. Cl.
    *F16L 37/08*         (2006.01)
    *A61M 39/10*       (2006.01)
    (Continued)

(52) U.S. Cl.
    CPC ........ *A61M 39/1011* (2013.01); *A61M 39/26* (2013.01); *F16L 37/08* (2013.01);
    (Continued)

(58) Field of Classification Search
    CPC .............................. F16L 37/0841; F16L 37/08
    (Continued)

(56) References Cited

U.S. PATENT DOCUMENTS 964,310 A     7/1910    Perazio
2,218,318 A    10/1940   Pfauser
(Continued)

FOREIGN PATENT DOCUMENTS

CA              1084551        8/1980

OTHER PUBLICATIONS

PCT International Patent Application No. PCT/US2017/014189, filed Jan. 19, 2017.

(Continued)

*Primary Examiner* — Aaron M Dunwoody
(74) *Attorney, Agent, or Firm* — Craig R. Miles; CR Miles P.C.

(57) ABSTRACT

Disclosed herein are embodiments of a connector system for releasably connecting together tubes, for example medical tubing, and methods of making and using such a connector system, whereby the connector system includes a female coupler having a first passageway; a male coupler having a second passageway; and a catch assembly comprising a catch movably coupled to the female coupler, a catch-biasing member which biases the catch, and a follower responsive to a cam, whereby the catch is responsive to the follower and correspondingly, the cam.

20 Claims, 16 Drawing Sheets

Related U.S. Application Data

(60) Provisional application No. 62/468,800, filed on Mar. 8, 2017.

(51) Int. Cl.
*A61M 39/26* (2006.01)
*F16L 37/36* (2006.01)

(52) U.S. Cl.
CPC ...... *F16L 37/36* (2013.01); *A61M 2039/1016* (2013.01); *A61M 2039/1027* (2013.01); *F17C 2205/037* (2013.01)

(58) Field of Classification Search
USPC .................... 285/33, 314–317, 394, 312
See application file for complete search history.

(56) References Cited

U.S. PATENT DOCUMENTS

| | | | |
|---|---|---|---|
| 2,263,293 | A * | 11/1941 | Ewald ............... F16L 37/0841 251/149.6 |
| 2,451,218 | A | 10/1948 | Hengst |
| 2,545,796 | A | 3/1951 | Scheiwer |
| 2,777,716 | A | 1/1957 | Gray |
| 2,805,089 | A | 9/1957 | Hansen |
| 2,854,259 | A | 9/1958 | Clark |
| 3,291,152 | A | 12/1966 | Comer |
| 3,460,801 | A | 8/1969 | Norton |
| 3,592,231 | A | 7/1971 | Lamb |
| 3,719,194 | A | 3/1973 | Anderson et al. |
| 3,847,413 | A | 11/1974 | Gurley et al. |
| 3,916,929 | A | 11/1975 | Brown |
| 4,220,174 | A | 9/1980 | Spitz |
| 4,436,125 | A | 3/1984 | Blenkush |
| 4,500,118 | A | 2/1985 | Blenkush |
| 4,541,457 | A | 9/1985 | Blenkush |
| 4,543,993 | A | 10/1985 | Calvin et al. |
| 4,576,359 | A | 3/1986 | Oetiker |
| 4,630,847 | A | 12/1986 | Blenkush |
| 4,703,957 | A | 11/1987 | Blenkush |
| 4,703,958 | A | 11/1987 | Fremy |
| 4,733,692 | A | 3/1988 | Kotake et al. |
| 4,819,692 | A | 4/1989 | Olson et al. |
| 4,877,145 | A | 10/1989 | Manner |
| 4,903,995 | A | 2/1990 | Blenkush et al. |
| 4,934,655 | A | 6/1990 | Blenkush et al. |
| 4,946,200 | A | 8/1990 | Blenkush et al. |
| 5,009,252 | A | 4/1991 | Faughn |
| 5,033,777 | A | 7/1991 | Blenkush |
| 5,052,725 | A | 10/1991 | Meyer et al. |
| 5,076,615 | A | 12/1991 | Sampson |
| 5,104,158 | A | 4/1992 | Meyer et al. |
| 5,165,733 | A | 11/1992 | Sampson |
| 5,178,303 | A | 1/1993 | Blenkush et al. |
| D339,417 | S | 9/1993 | Sampson et al. |
| 5,259,894 | A | 11/1993 | Sampson |
| 5,295,339 | A | 3/1994 | Manner |
| 5,316,041 | A | 5/1994 | Ramacier, Jr. et al. |
| 5,353,836 | A | 10/1994 | deCler et al. |
| 5,390,702 | A | 2/1995 | Smith, III |
| D357,307 | S | 4/1995 | Ramacier, Jr. et al. |
| 5,460,413 | A | 10/1995 | Sampson |
| 5,494,074 | A | 2/1996 | Ramacier, Jr. et al. |
| 5,529,085 | A | 6/1996 | Richards et al. |
| D372,093 | S | 7/1996 | Sampson et al. |
| D375,160 | S | 10/1996 | Sampson et al. |
| 5,564,752 | A | 10/1996 | Sampson |
| 5,639,064 | A | 6/1997 | deCler et al. |
| D384,731 | S | 10/1997 | Ramacier, Jr. et al. |
| 5,695,221 | A | 12/1997 | Sunderhaus |
| D388,876 | S | 1/1998 | Sampson |
| 5,704,106 | A | 1/1998 | Sampson et al. |
| 5,799,987 | A | 9/1998 | Sampson |
| 5,820,614 | A | 10/1998 | Erskine et al. |
| 5,826,610 | A | 10/1998 | Bodhaine |
| 5,845,943 | A | 12/1998 | Ramacier, Jr. et al. |
| 5,848,811 | A | 12/1998 | Sampson |
| 5,848,997 | A | 12/1998 | Erskine et al. |
| 5,869,803 | A | 2/1999 | Noguchi et al. |
| 5,911,403 | A | 6/1999 | deCler et al. |
| 5,937,885 | A | 8/1999 | Sampson |
| 5,938,244 | A | 8/1999 | Meyer |
| 5,975,489 | A | 11/1999 | deCler et al. |
| 6,024,124 | A | 2/2000 | Braun et al. |
| 6,082,401 | A | 7/2000 | Braun et al. |
| 6,095,191 | A | 8/2000 | Smith, III |
| 6,146,374 | A | 11/2000 | Erskine et al. |
| 6,161,578 | A | 12/2000 | Braun et al. |
| 6,206,040 | B1 | 3/2001 | Smith, III |
| 6,231,089 | B1 | 5/2001 | deCler et al. |
| 6,382,593 | B1 | 5/2002 | deCler et al. |
| 6,412,829 | B1 | 7/2002 | Persson |
| 6,511,100 | B1 | 1/2003 | Le Clinche |
| 6,581,907 | B1 | 6/2003 | Kuwabara et al. |
| 6,626,419 | B2 | 9/2003 | deCler et al. |
| 6,649,829 | B2 | 11/2003 | Garber et al. |
| 6,705,591 | B2 | 3/2004 | deCler |
| 6,848,602 | B2 | 2/2005 | deCler et al. |
| 6,871,669 | B2 | 3/2005 | Meyer et al. |
| D503,778 | S | 4/2005 | Wicks |
| 6,897,374 | B2 | 5/2005 | Garber et al. |
| 6,902,144 | B2 | 6/2005 | deCler |
| 6,916,007 | B2 | 7/2005 | deCler et al. |
| 6,962,275 | B2 | 11/2005 | deCler et al. |
| 6,978,800 | B2 | 12/2005 | deCler et al. |
| 7,080,665 | B2 | 7/2006 | Whall |
| 7,163,022 | B2 | 1/2007 | Whall |
| 7,316,424 | B2 | 1/2008 | Kardeis et al. |
| 7,394,375 | B2 | 7/2008 | Johnson |
| 7,434,842 | B2 | 10/2008 | Schmidt |
| 7,448,653 | B2 | 11/2008 | Jensen et al. |
| 7,469,472 | B2 | 12/2008 | deCler et al. |
| 7,488,446 | B2 | 2/2009 | Meyer et al. |
| 7,514,025 | B2 | 4/2009 | Hofmann et al. |
| 7,546,857 | B2 | 6/2009 | Chadbourne et al. |
| 7,547,047 | B2 | 6/2009 | deCler et al. |
| 7,562,906 | B2 | 7/2009 | Schmidt |
| D602,128 | S | 10/2009 | Williams et al. |
| 7,631,660 | B2 | 12/2009 | deCler et al. |
| 7,647,954 | B2 | 1/2010 | Garber et al. |
| D612,019 | S | 3/2010 | Williams et al. |
| D612,021 | S | 3/2010 | Schmidt |
| 7,695,020 | B2 | 4/2010 | Schmidt |
| 7,708,025 | B2 | 5/2010 | Johnson |
| 7,757,974 | B2 | 7/2010 | Hofmann et al. |
| 7,770,939 | B2 | 8/2010 | Jensen et al. |
| 7,806,139 | B2 | 10/2010 | Packham et al. |
| 7,828,336 | B2 | 11/2010 | Gammons |
| 7,841,357 | B2 | 11/2010 | Rankin |
| D629,894 | S | 12/2010 | Lombardi, III et al. |
| D630,320 | S | 1/2011 | Lombardi, III et al. |
| 7,875,346 | B2 | 1/2011 | Hofmann et al. |
| 7,878,553 | B2 | 2/2011 | Wicks et al. |
| D634,840 | S | 3/2011 | Lombardi, III et al. |
| D639,398 | S | 6/2011 | Wilhelm |
| 7,954,374 | B2 | 6/2011 | Rankin |
| 7,954,515 | B2 | 6/2011 | Gerst |
| D642,244 | S | 7/2011 | Wilhelm |
| 7,976,072 | B2 | 7/2011 | Parrish |
| D645,547 | S | 9/2011 | Lombardi et al. |
| D649,240 | S | 11/2011 | Lewis et al. |
| D649,938 | S | 12/2011 | Erickson et al. |
| D649,939 | S | 12/2011 | Erickson et al. |
| D650,478 | S | 12/2011 | Lewis |
| D652,510 | S | 1/2012 | Lombardi, III et al. |
| D652,511 | S | 1/2012 | Lombardi, III et al. |
| D654,573 | S | 2/2012 | Lombardi, III et al. |
| 8,113,546 | B2 | 2/2012 | Jensen et al. |
| D655,393 | S | 3/2012 | Whitaker |
| 8,162,242 | B2 | 4/2012 | Hofmann et al. |
| D663,022 | S | 7/2012 | Lombardi, III et al. |
| 8,235,426 | B2 | 8/2012 | Pisula, Jr. et al. |
| 8,256,803 | B2 | 9/2012 | Takahashi |
| 8,388,873 | B2 | 3/2013 | Hofmann et al. |

(56) References Cited

U.S. PATENT DOCUMENTS

| | | |
|---|---|---|
| 8,397,756 B2 | 3/2013 | Packham et al. |
| 8,448,994 B2 | 5/2013 | Pisula, Jr. et al. |
| RE44,310 E | 6/2013 | Chadbourne et al. |
| 8,491,016 B2 | 7/2013 | Williams et al. |
| 8,596,688 B2 | 12/2013 | Pisula, Jr. et al. |
| D698,440 S | 1/2014 | Lombardi, III et al. |
| D699,841 S | 2/2014 | Lombardi, III et al. |
| 8,684,035 B2 | 4/2014 | Bernhard |
| D712,537 S | 9/2014 | Lombardi et al. |
| 8,897,756 B2 | 11/2014 | Skog et al. |
| 8,945,091 B2 | 2/2015 | Williams et al. |
| D724,703 S | 3/2015 | Downs |
| 9,027,968 B2 | 5/2015 | Gerst |
| 9,046,205 B2 | 6/2015 | Whitaker et al. |
| 9,157,560 B2 | 10/2015 | Rehder et al. |
| 9,266,257 B2 | 2/2016 | Hofmann et al. |
| 9,279,530 B2 | 3/2016 | Schmidt |
| 9,364,653 B2 | 6/2016 | Williams et al. |
| 9,371,921 B2 | 6/2016 | Whitaker |
| D761,395 S | 7/2016 | Plackner et al. |
| 9,388,929 B2 | 7/2016 | Lewis et al. |
| D762,826 S | 8/2016 | Plackner et al. |
| 9,464,741 B2 | 10/2016 | Lewis et al. |
| 9,498,800 B2 | 11/2016 | Hofmann et al. |
| 9,506,590 B2 | 11/2016 | Wilhelm et al. |
| 10,350,401 B2 | 7/2019 | Ciccone et al. |
| 2001/0035220 A1 | 11/2001 | Russell |
| 2002/0011730 A1 | 1/2002 | Stickan |
| 2002/0014608 A1 | 2/2002 | deCler et al. |
| 2002/0063427 A1 | 5/2002 | Schiemann et al. |
| 2002/0074533 A1 | 6/2002 | DeCler et al. |
| 2002/0101076 A1 | 8/2002 | Barrier |
| 2002/0129858 A1 | 9/2002 | Meyer et al. |
| 2002/0170731 A1 | 11/2002 | Garber et al. |
| 2002/0190453 A1 | 12/2002 | Wilhelm et al. |
| 2003/0042734 A1 | 3/2003 | Kuwabara |
| 2003/0062498 A1 | 4/2003 | DeCler et al. |
| 2003/0062501 A1 | 4/2003 | DeCler |
| 2003/0196703 A1 | 10/2003 | DeCler et al. |
| 2004/0016900 A1 | 1/2004 | Kouda |
| 2004/0079423 A1 | 4/2004 | Mikiya et al. |
| 2004/0130438 A1 | 7/2004 | Garber |
| 2004/0169368 A1 | 9/2004 | Garber et al. |
| 2004/0173769 A1 | 9/2004 | DeCler |
| 2004/0222180 A1 | 11/2004 | Wicks et al. |
| 2004/0232175 A1 | 11/2004 | DeCler et al. |
| 2005/0001425 A1 | 1/2005 | DeCler et al. |
| 2005/0012330 A1 | 1/2005 | Schmidt |
| 2005/0057042 A1 | 3/2005 | Wicks |
| 2005/0076964 A1 | 4/2005 | Whall |
| 2005/0082828 A1 | 4/2005 | Wicks et al. |
| 2005/0084410 A1 | 4/2005 | Meyer et al. |
| 2005/0127117 A1 | 6/2005 | deCler et al. |
| 2005/0211934 A1 | 9/2005 | Garber et al. |
| 2005/0237241 A1 | 10/2005 | Garber et al. |
| 2005/0247371 A1 | 11/2005 | Chadbourne et al. |
| 2006/0048849 A1 | 3/2006 | DeCler |
| 2006/0076419 A1 | 4/2006 | Johnson |
| 2006/0138704 A1 | 6/2006 | DeCler et al. |
| 2006/0186233 A1 | 8/2006 | Holm et al. |
| 2006/0196556 A1 | 9/2006 | Johnson |
| 2006/0207345 A1 | 9/2006 | Rankin |
| 2006/0231137 A1 | 10/2006 | Whall |
| 2007/0001452 A1 | 1/2007 | Friel |
| 2007/0025811 A1 | 2/2007 | Wilhelm |
| 2007/0169825 A1 | 7/2007 | Packham et al. |
| 2007/0209716 A1 | 9/2007 | Rankin |
| 2007/0259246 A1 | 11/2007 | Jang et al. |
| 2008/0001395 A1 | 1/2008 | Kouda |
| 2008/0011785 A1 | 1/2008 | Braun et al. |
| 2008/0061553 A1 | 3/2008 | Schmidt |
| 2008/0067807 A1 | 3/2008 | DeCler et al. |
| 2008/0191069 A1 | 8/2008 | Hofmann et al. |
| 2008/0277924 A1 | 11/2008 | Jensen et al. |
| 2009/0021007 A1 | 1/2009 | Le Bars et al. |
| 2009/0167018 A1* | 7/2009 | Lien ............... F16L 37/38 285/308 |
| 2009/0188575 A1 | 7/2009 | Williams et al. |
| 2009/0256355 A1 | 10/2009 | Wicks et al. |
| 2009/0261582 A1* | 10/2009 | Gaudin ............ F16L 37/0841 285/321 |
| 2009/0284007 A1 | 11/2009 | Schmidt |
| 2010/0001516 A1 | 1/2010 | Pisula, Jr. et al. |
| 2010/0006157 A1 | 1/2010 | Gerst |
| 2010/0006162 A1 | 1/2010 | Rankin |
| 2010/0019487 A1 | 1/2010 | deCler et al. |
| 2010/0043988 A1 | 2/2010 | Hofmann et al. |
| 2010/0127492 A1* | 5/2010 | Poder ............... F16L 37/0841 285/93 |
| 2010/0155979 A1 | 6/2010 | Hofmann et al. |
| 2010/0230950 A1 | 9/2010 | Williams et al. |
| 2010/0295295 A1 | 11/2010 | Schmidt |
| 2010/0301599 A1 | 12/2010 | Jensen et al. |
| 2011/0012340 A1 | 1/2011 | Packham et al. |
| 2011/0062701 A1 | 3/2011 | Downs et al. |
| 2011/0121035 A1 | 5/2011 | Greter et al. |
| 2011/0127767 A1 | 6/2011 | Wicks et al. |
| 2011/0204621 A1 | 8/2011 | Whitaker et al. |
| 2011/0204622 A1* | 8/2011 | Lewis ............... F16L 37/0841 285/313 |
| 2011/0210541 A1* | 9/2011 | Lewis ............... F16L 37/0841 285/317 |
| 2012/0031515 A1 | 2/2012 | Whitaker |
| 2012/0068457 A1 | 3/2012 | Pisula, Jr. et al. |
| 2012/0161051 A1 | 6/2012 | Williams et al. |
| 2012/0179052 A1 | 7/2012 | Wilhelm et al. |
| 2012/0259237 A1 | 10/2012 | Axelrod |
| 2013/0030387 A1 | 1/2013 | Williams et al. |
| 2013/0092271 A1 | 4/2013 | Downs et al. |
| 2013/0099489 A1 | 4/2013 | Williams et al. |
| 2013/0207380 A1 | 8/2013 | Williams et al. |
| 2013/0289517 A1 | 10/2013 | Williams et al. |
| 2013/0333767 A1 | 12/2013 | Schmidt |
| 2014/0060675 A1 | 3/2014 | Wilhelm et al. |
| 2014/0117664 A1 | 5/2014 | Ekstrom |
| 2014/0260554 A1 | 9/2014 | Rankin |
| 2014/0261819 A1 | 9/2014 | Vranish |
| 2015/0028586 A1 | 1/2015 | Gerst et al. |
| 2015/0076815 A1 | 3/2015 | Lombardi, III et al. |
| 2015/0090915 A1 | 4/2015 | Vranish |
| 2015/0135502 A1 | 5/2015 | Rankin et al. |
| 2015/0231369 A1 | 8/2015 | Gray et al. |
| 2015/0260325 A1 | 9/2015 | Quick |
| 2016/0047503 A1 | 2/2016 | Ballard et al. |

OTHER PUBLICATIONS

U.S. Appl. No. 15/912,280, filed Mar. 5, 2018.
PCT International Patent Application No. PCT/US18/21467; International Search Report and Written Opinion of the International Searching Authority dated Jun. 1, 2018, 9 pages.
Eldon James. Introducing SeriesLock™ the Spring-Free Flow Path Quick Disconnect Coupler (with video). Website, https://www.eldonjames.com/serieslock-quick-disconnect-coupler/, originally downloaded Jun. 6, 2018, 5 pages.

* cited by examiner

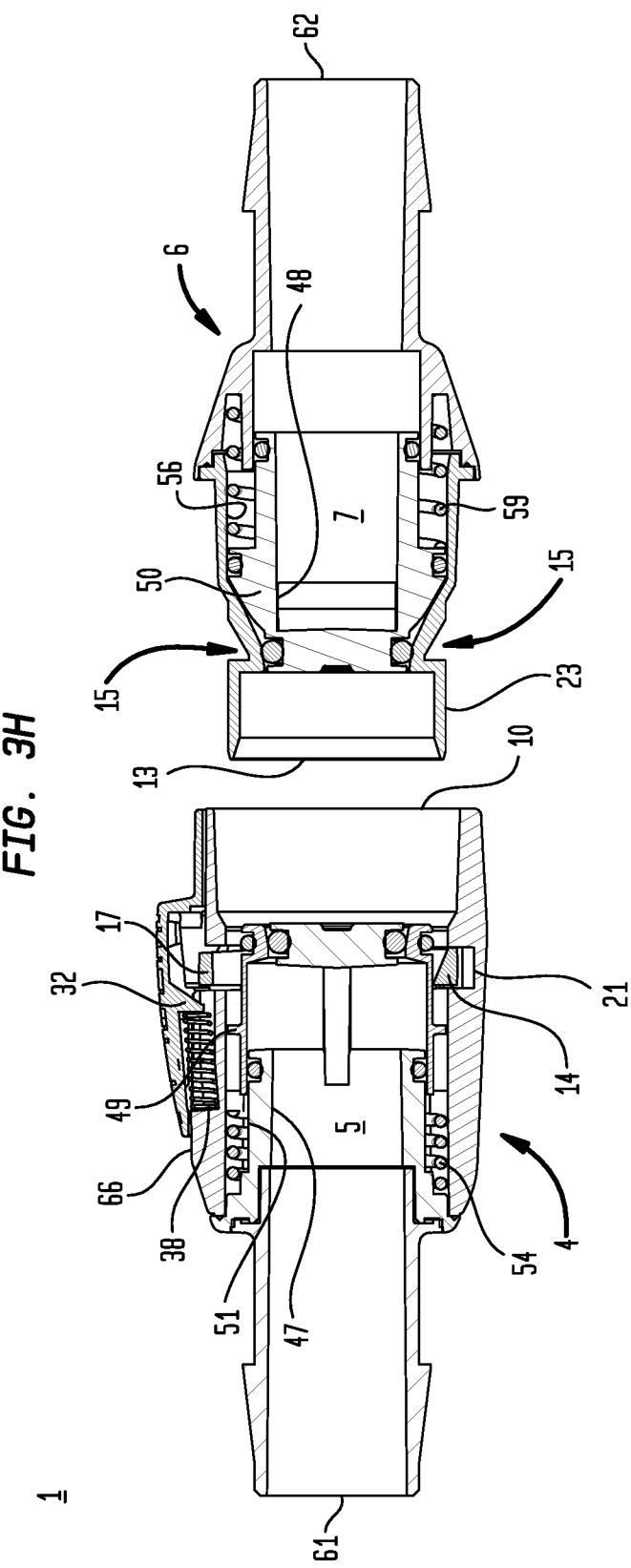

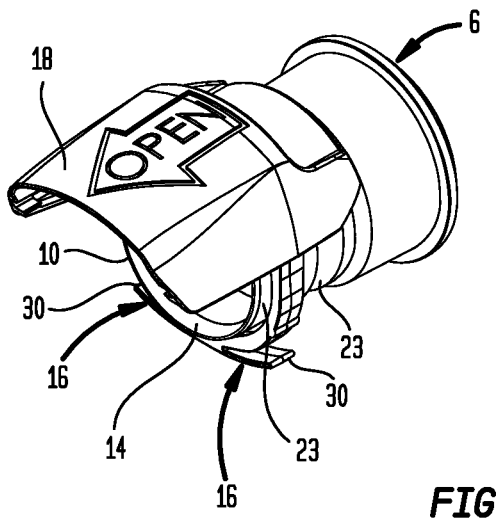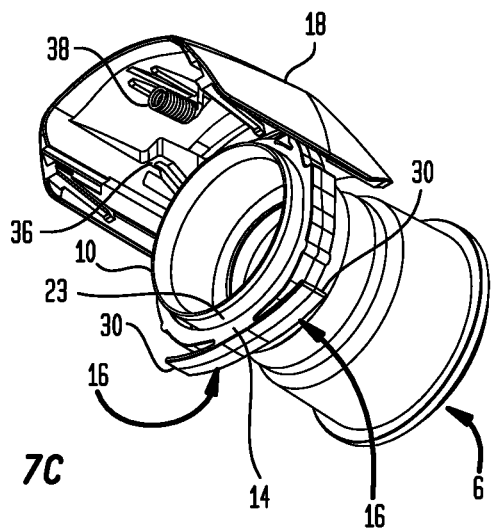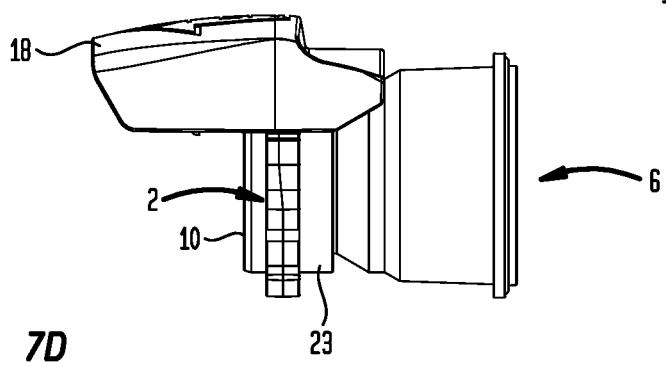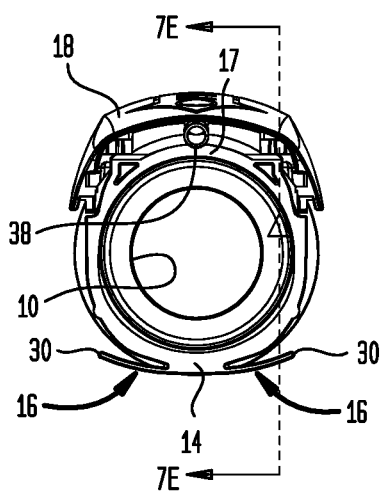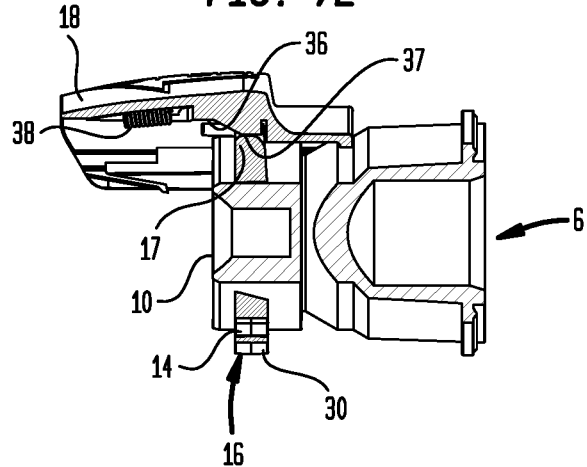

CATCH ASSEMBLY FOR RELEASABLY CONNECTING FLUID CONDUITS

This United States Patent Application is a continuation of U.S. patent application Ser. No. 15/912,280, filed Mar. 5, 2018, now U.S. Pat. No. 10,350,401, issued Jul. 16, 2019, which claims the benefit of U.S. Provisional Patent Application No. 62/468,800, filed Mar. 8, 2017, each hereby incorporated by reference herein.

I. SUMMARY OF THE INVENTION

A broad object of a particular embodiment of the invention can be to provide a connector system for releasably connecting together tubes, for example medical tubing, and methods of making and using such a connector system, whereby the connector system includes a female coupler having a first passageway; a male coupler having a second passageway; and a catch assembly comprising a catch movably coupled to the female coupler, a catch-biasing member which biases the catch, and a follower responsive to a cam, whereby the catch is responsive to the follower and correspondingly, the cam.

Naturally, further objects of the invention are disclosed throughout other areas of the specification, drawings, and claims.

II. A BRIEF DESCRIPTION OF THE DRAWINGS

FIG. 3H is a cross-sectional view of the particular embodiment of the connector system shown in FIG. 3F.

FIG. 3I is a cross-sectional view of the particular embodiment of the connector system shown in FIG. 3D.

FIG. 3J is a cross-sectional view of the particular embodiment of the connector system shown in FIG. 3D.

FIG. 7A is a perspective view of isolated components of the particular embodiment of the connector system shown in FIG. 6A.

FIG. 7B is a perspective view of isolated components of the particular embodiment of the connector system shown in FIG. 6A.

FIG. 7C is a first side view of isolated components of the particular embodiment of the connector system shown in FIG. 6A.

FIG. 7D is a first end view of isolated components of the particular embodiment of the connector system shown in FIG. 6A.

FIG. 7E is a cross-sectional view of the particular embodiment of the connector system shown in FIG. 7D.

III. DETAILED DESCRIPTION OF THE PREFERRED EMBODIMENTS

Figure 1:
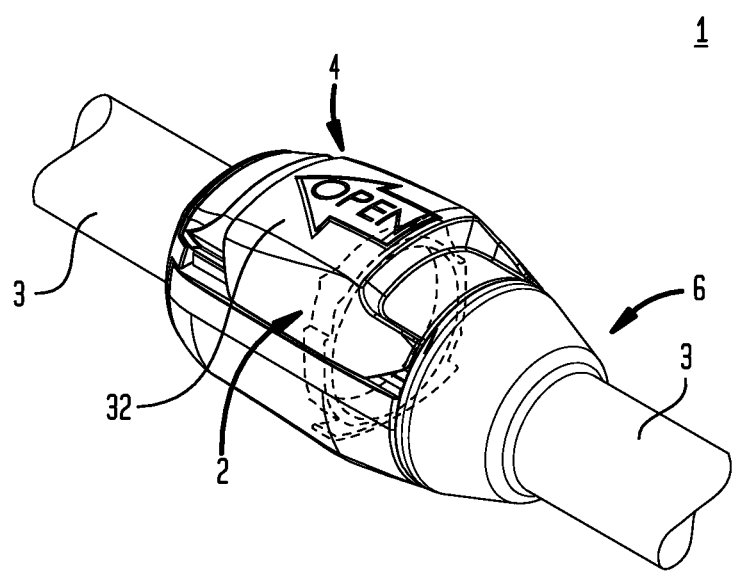
FIG. 1 is an illustration of a method of using a particular embodiment of the connector system, whereby female and male couplers are releasably matably engaged to dispose in a connected condition.

Now referring primarily to FIG. 1, which illustrates a method of using a particular embodiment of a connector system (1) including an inventive catch assembly (2) for releasably connecting together tubes (3), such as medical tubing employed in a bio-medical environment. Advantageously, the connector system (1) can be relatively easily and securely connected, and yet relatively easily intentionally disconnected.

Generally, the connector system (1) includes a female coupler (4) having a first passageway (5) and a male coupler (6) having a second passageway (7). Upon releasable matable axial (or longitudinal) coupling of the female and male couplers (4)(6) (or, stated more concisely, upon connection of the female and male couplers (4)(6)), a connected condition of the connector system (1) is achieved, disposing the first and second passageways (5)(7) in fluidic communication to provide a fluid flow path (9).

For the purposes of the present invention, a longitudinal direction can be considered generally parallel to the first passageway (5), the second passageway (7), and/or the fluid flow path (9).

Figure 3A:
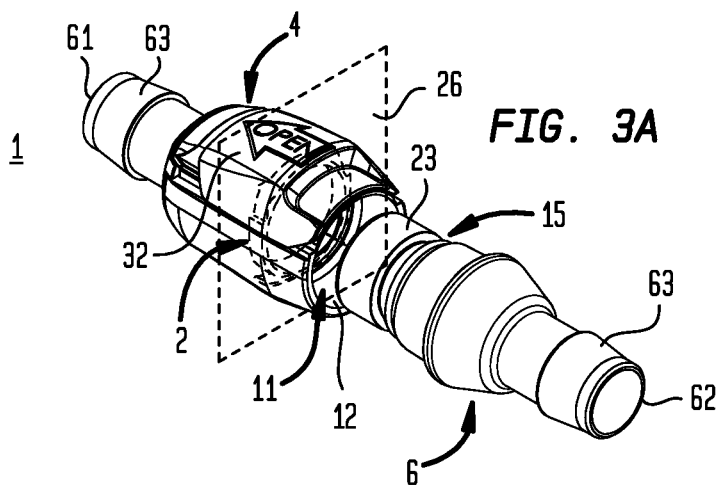
FIG. 3A is a perspective view of a particular embodiment of the connector system, whereby female and male couplers are in adjacent axial relation but are not releasably matably engaged, thus disposing in a disconnected condition.
Figure 3B:
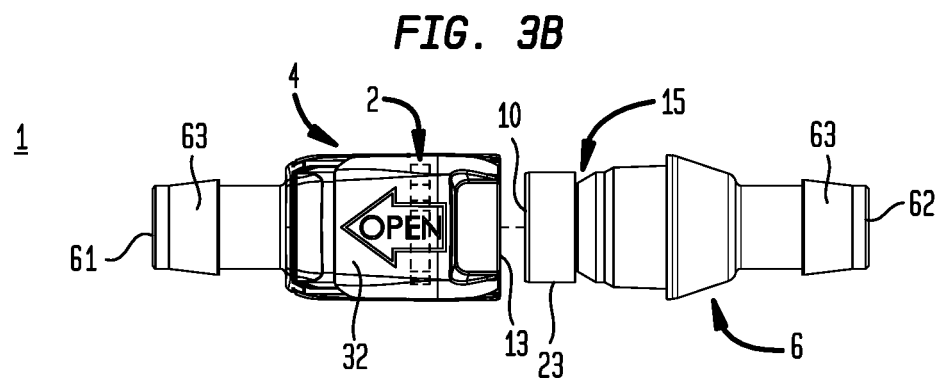
FIG. 3B is a top view of the particular embodiment of the connector system shown in FIG. 3A.
Figure 3C:
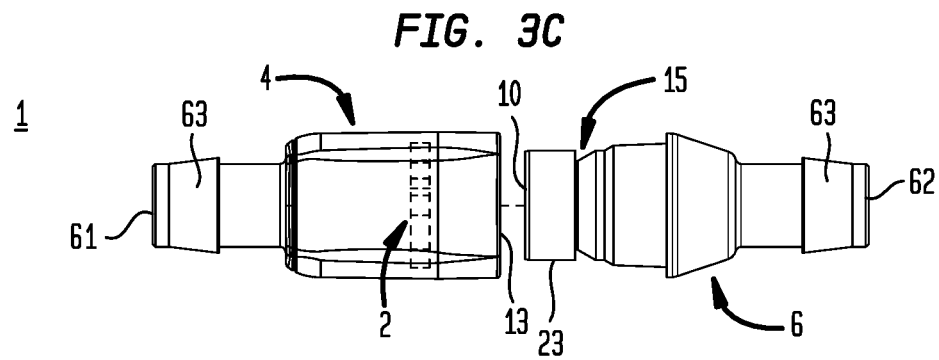
FIG. 3C is a bottom view of the particular embodiment of the connector system shown in FIG. 3A.
Figure 3D:
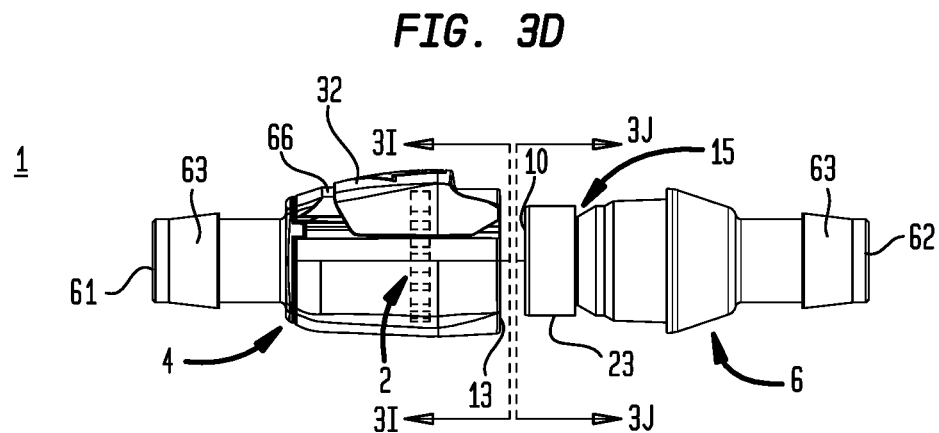
FIG. 3D is a first side view of the particular embodiment of the connector system shown in FIG. 3A.
Figure 3E:
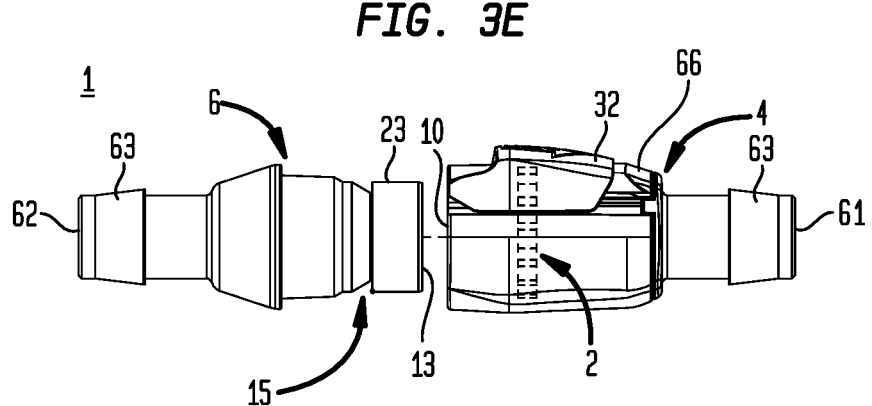
FIG. 3E is a second side view of the particular embodiment of the connector system shown in FIG. 3A.
Figure 3F:
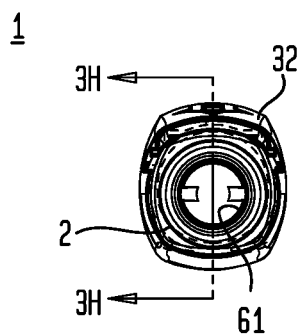
FIG. 3F is a first end view of the particular embodiment of the connector system shown in FIG. 3A.
Figure 3G:
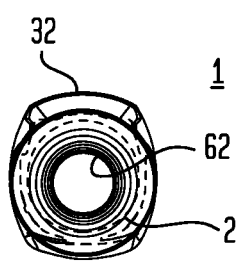
FIG. 3G is a second end view of the particular embodiment of the connector system shown in FIG. 3A.

Now more specifically, to achieve the connected condition of the connector system (1), a male coupler matable end (10) of the male coupler (6) can be matably received within a female coupler inner space (11) of the female coupler (4), whereby the female coupler inner space (11) can be defined by a female coupler inner surface (12) proximate a female coupler matable end (13) (as shown in the example of FIG. 3A).

The connector system (1) further includes an inventive catch assembly (2) comprising a catch (14) movably coupled to the female coupler (4) and a catch-receiving element (15) coupled to the male coupler (6). Upon connection of the female and male couplers (4)(6), the catch (14) engages with the catch-receiving element (15) to fix an axial position of the female coupler (4) in relation to the male coupler (6), thereby achieving the connected condition of the connector system (1).

For the purposes of the present invention, the term "catch" means a restraint which, upon matable engagement with a catch-receiving element (15), can function to partially or completely restrain travel of an associated component, such as a female coupler (4).

For the purposes of the present invention, the term "catch-receiving element" means a restraint which, upon matable engagement with a catch (14), can function to partially or completely restrain travel of an associated component, such as a male coupler (6).

Now referring primarily to FIG. 2H, FIG. 3H, FIG. 4B, FIG. 5A through FIG. 5E, FIG. 6B, FIG. 7A through FIG. 7E, and FIG. 8A through FIG. 9C, the catch assembly (2) can comprise a catch (14), a catch-biasing member (16) which can bias the catch (14), and a follower (17) which can be responsive to a cam (18). The catch (14) can be responsive to the follower (17) and correspondingly, the catch (14) can be responsive to the cam (18).

For the purposes of the present invention, the term "cam" means a movable element in a mechanical linkage, whereby the cam (18) can have an irregular periphery and may be useful in transforming motion, for example transforming motion in a first direction into motion in a second direction.

For the purposes of the present invention, the term "follower" means a movable element in a mechanical linkage, whereby movement of the follower (17) results from movement of the cam (18).

Figure 4A:
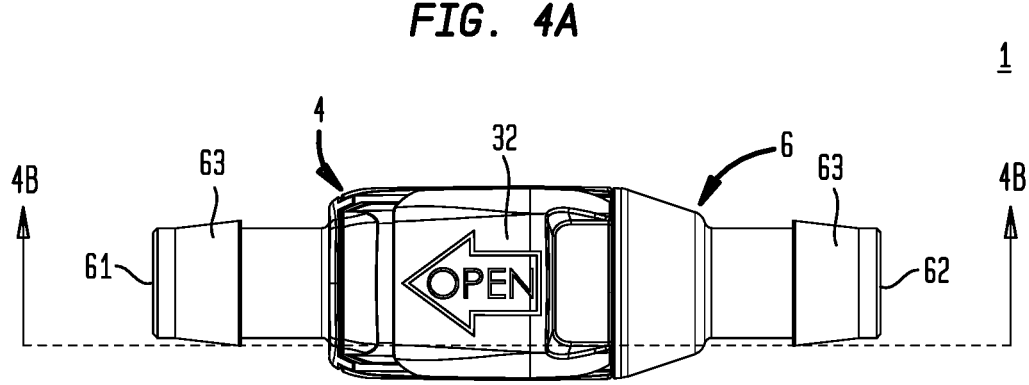
FIG. 4A is a top view of a particular embodiment of the connector system, whereby female and male couplers are releasably matably engaged to dispose in a connected condition, and whereby the release element disposes in a first position.
Figure 4B:
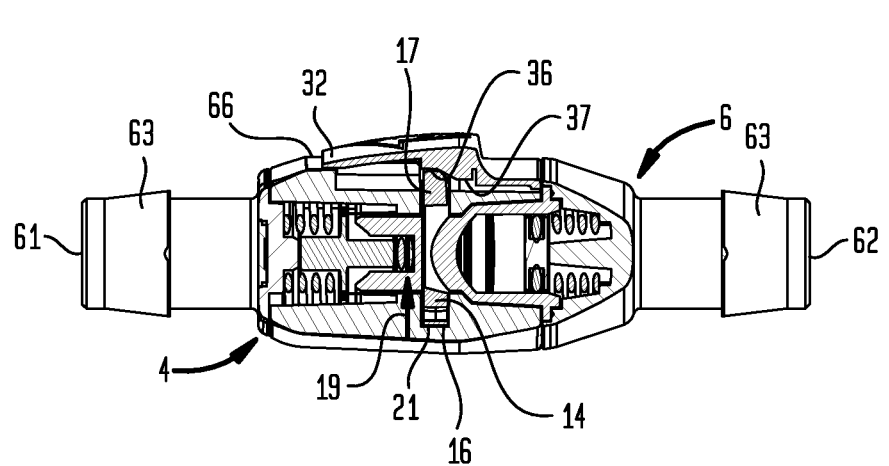
FIG. 4B is a cross-sectional view of the particular embodiment of the connector system shown in FIG. 4A.
Figure 5A:
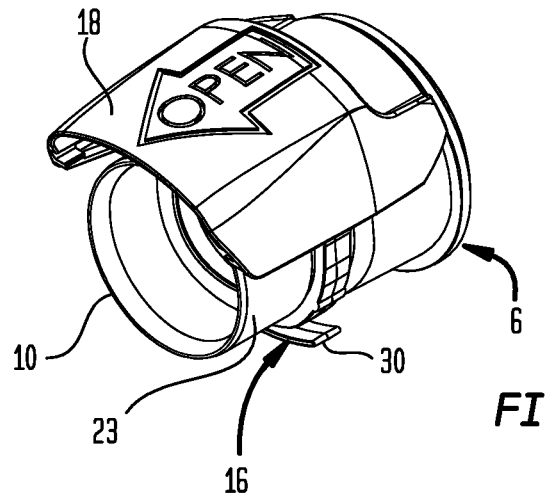
FIG. 5A is a perspective view of isolated components of the particular embodiment of the connector system shown in FIG. 4A.
Figure 5B:
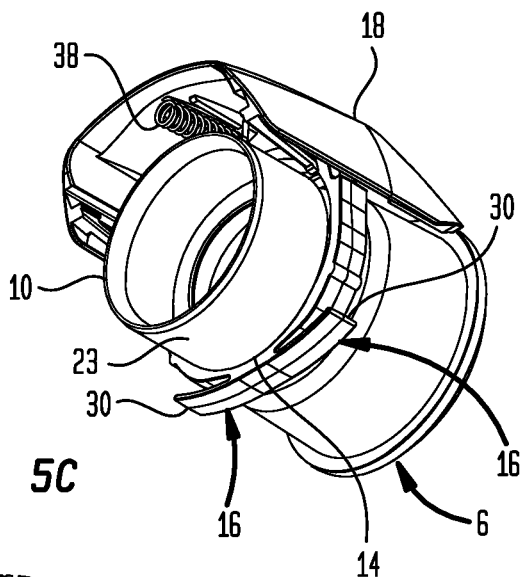
FIG. 5B is a perspective view of isolated components of the particular embodiment of the connector system shown in FIG. 4A.
Figure 5C:
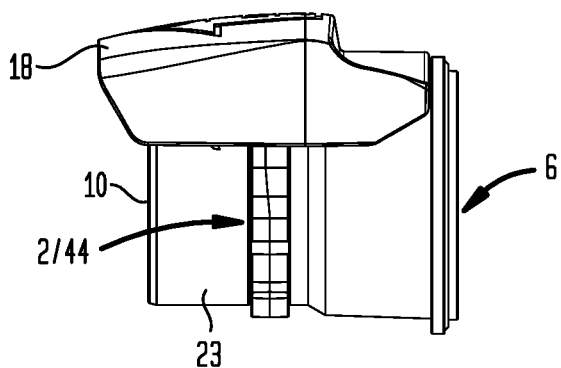
FIG. 5C is a first side view of isolated components of the particular embodiment of the connector system shown in FIG. 4A.
Figure 5D:
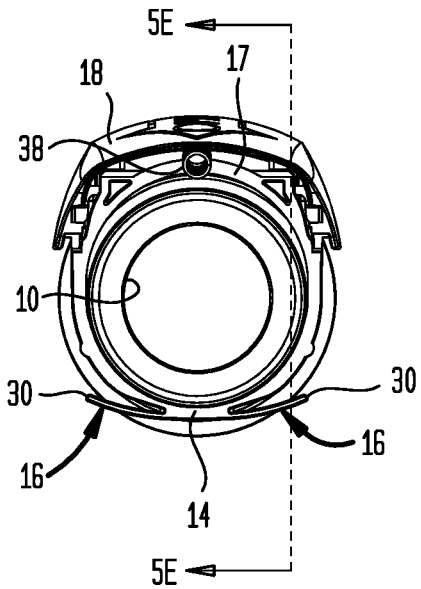
FIG. 5D is a first end view of isolated components of the particular embodiment of the connector system shown in FIG. 4A.
Figure 5E:
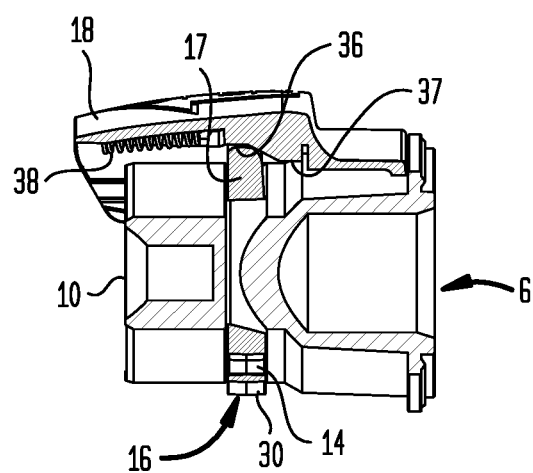
FIG. 5E is a cross-sectional view of the particular embodiment of the connector system shown in FIG. 5D.
Figure 6A:
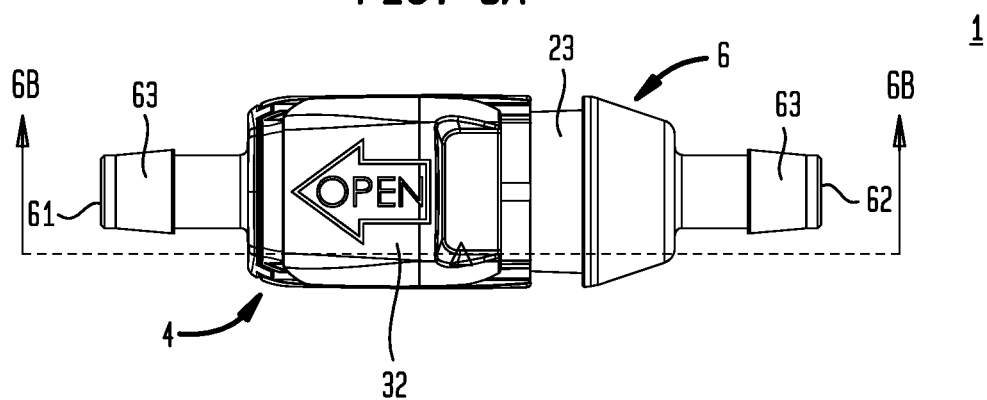
FIG. 6A is a top view of a particular embodiment of the connector system, whereby female and male couplers are in adjacent axial relation but are not releasably matably engaged, thus disposing in a disconnected condition, and whereby the release element disposes in a second position.
Figure 6B:
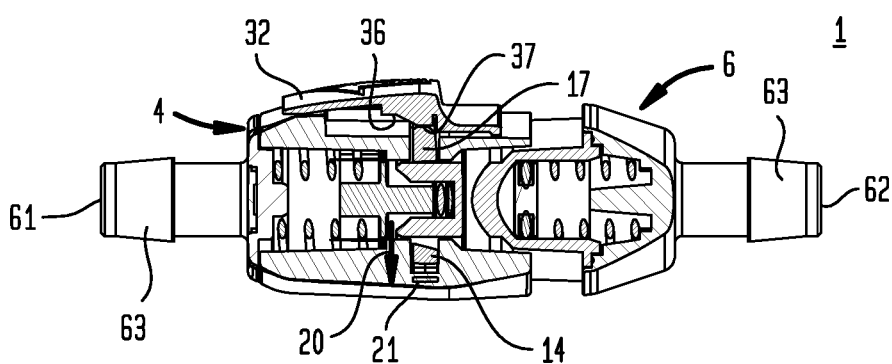
FIG. 6B is a cross-sectional view of the particular embodiment of the connector system shown in FIG. 6A.
Figure 8A:
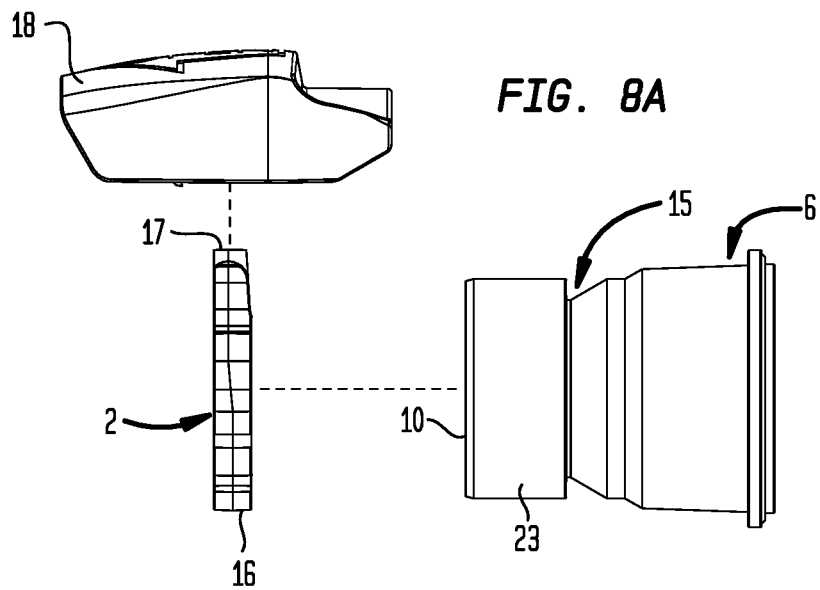
FIG. 8A is an exploded first side view of isolated components of a particular embodiment of the connector system.
Figure 8B:
FIG. 8B is a perspective view of the particular embodiment of the connector system shown in FIG. 8A.
Figure 8C:
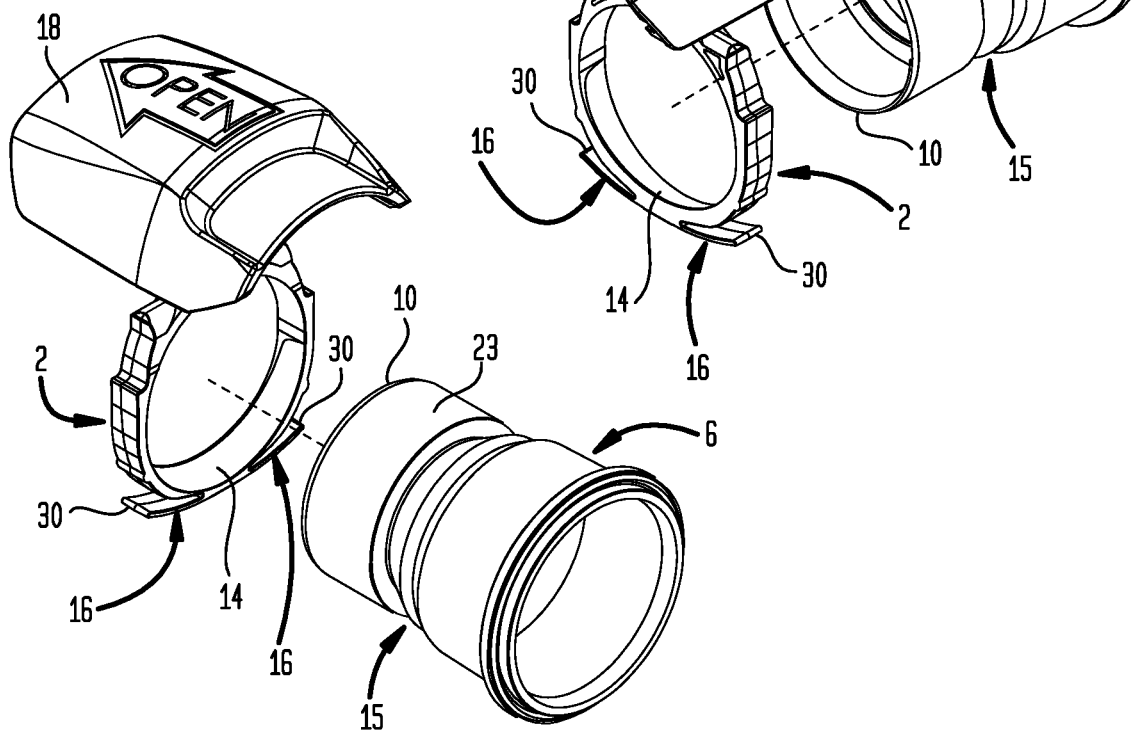
FIG. 8C is a perspective view of the particular embodiment of the connector system shown in FIG. 8A.
Figure 8D:
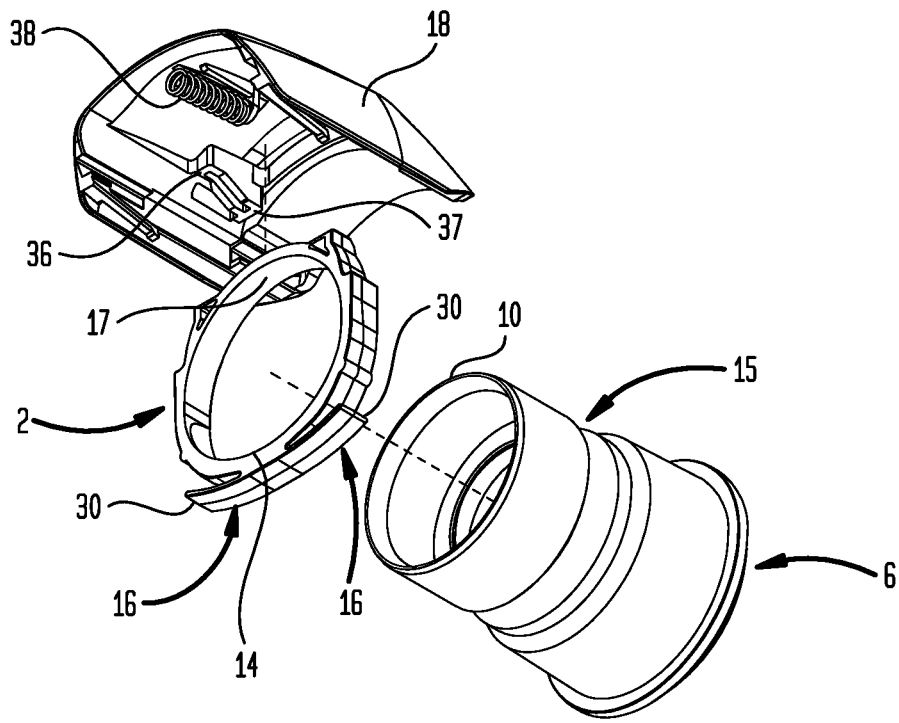
FIG. 8D is a perspective view of the particular embodiment of the connector system shown in FIG. 8A.
Figure 8E:
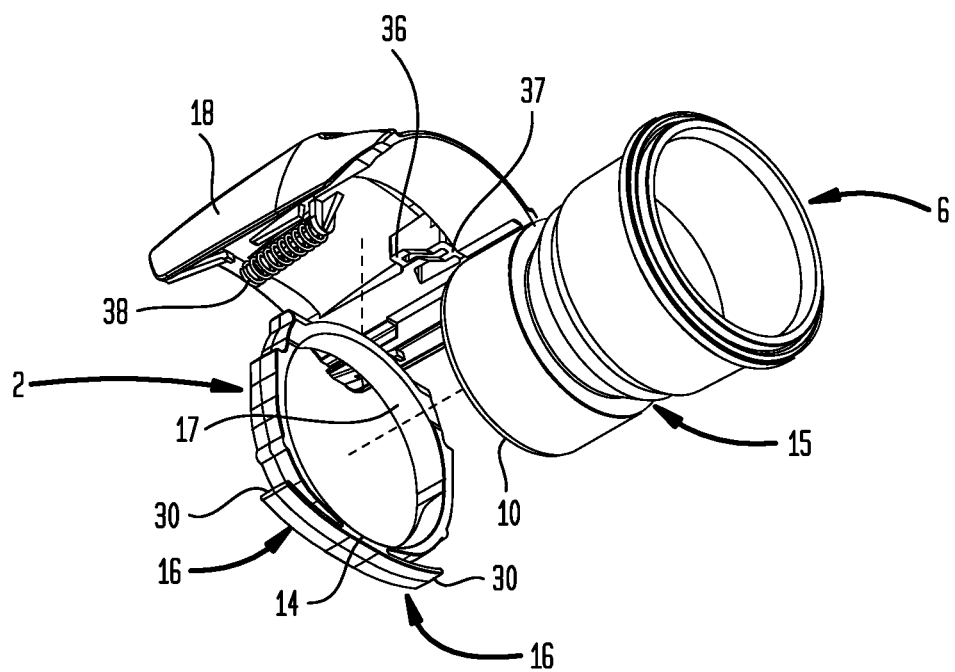
FIG. 8E is a perspective view of the particular embodiment of the connector system shown in FIG. 8A.

The catch assembly (2) can be movably coupled to the female coupler (4) such that the catch (14) can move inwardly toward or into the female coupler inner space (11) as illustrated by the first arrow (19) shown in FIG. 4B, or the catch (14) can move outwardly away from or out of the female coupler inner space (11) as illustrated by the second arrow (20) shown in FIG. 6B.

Further, the catch assembly (2) can be movably coupled to the female coupler inner surface (12) which defines the female coupler inner space (11). As but one illustrative example, the catch (14) can be movably disposed within a channel (21) inset within the female coupler inner surface (12), whereby the channel (21) communicates with the female coupler inner space (11). When a majority of the catch (14) or the entirety of the catch (14) is received within the channel (21), the catch (14) can dispose outwardly and away from the female coupler inner space (11). Conversely, when the catch (14) moves inwardly toward or into the female coupler inner space (11), a majority of the catch (14) or the entirety of the catch (14) can dispose outside of the channel (21).

Now referring primarily to FIG. 3A through FIG. 3E, FIG. 3H, and FIG. 8A through FIG. 9C, the catch-receiving element (15) can be configured as a retention groove (22) coupled to the male coupler matable end (10). For example, the retention groove (22) can be disposed within a male coupler outer surface (23) proximate the male coupler matable end (10).

As to particular embodiments, the retention groove (22) can be configured as a circumferential retention groove (22) extending around the male coupler outer surface (23) proximate the male coupler matable end (10).

Thus, upon matable reception of the male coupler matable end (10) within the female coupler inner space (11), the retention groove (22) can align with the channel (21) and the catch (14) can move outwardly from the channel (21) and inwardly toward the female coupler inner space (11) for engagement with the retention groove (22), thereby disposing the catch (14) in an engaged condition (24) to fix an axial position of the female coupler (4) in relation to the male coupler (6).

In contrast, the catch (14) can move outwardly from the female coupler inner space (11) and into the channel (21) to dispose the catch (14) in a disengaged condition (25) wherein the catch (14) is disengaged from the retention groove (22), allowing the female and male couplers (4)(6) to disconnect by axial movement away from one another.

Figure 2A:
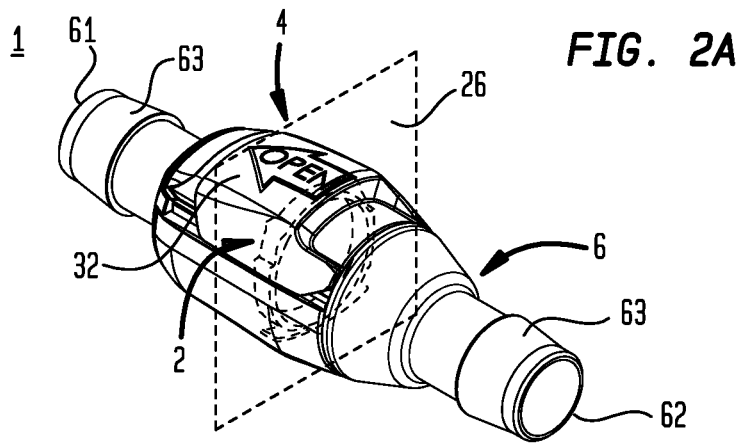
FIG. 2A is a perspective view of a particular embodiment of the connector system, whereby female and male couplers are releasably matably engaged to dispose in a connected condition.
Figure 2B:
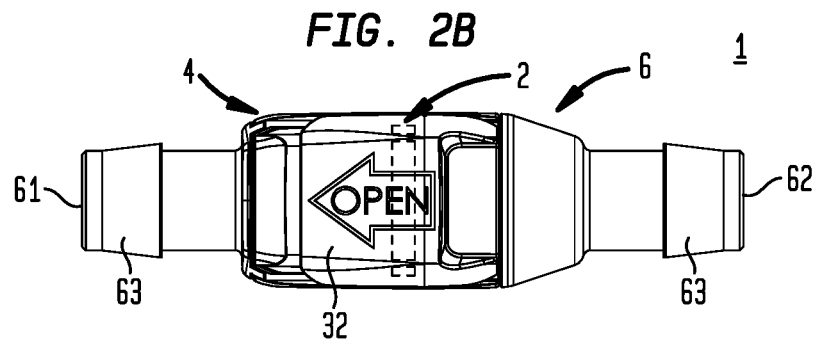
FIG. 2B is a top view of the particular embodiment of the connector system shown in FIG. 2A.
Figure 2C:
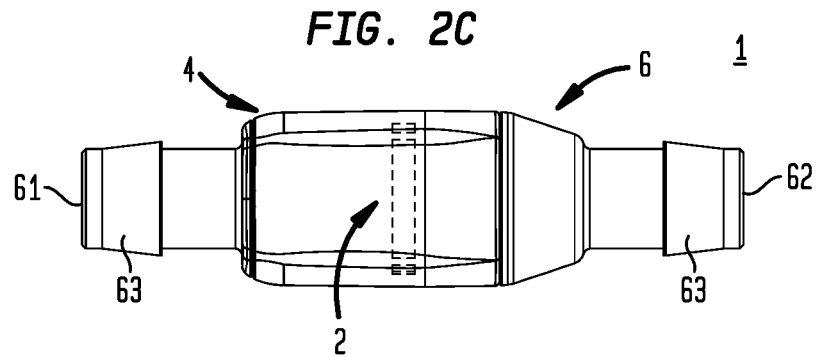
FIG. 2C is a bottom view of the particular embodiment of the connector system shown in FIG. 2A.
Figure 2D:
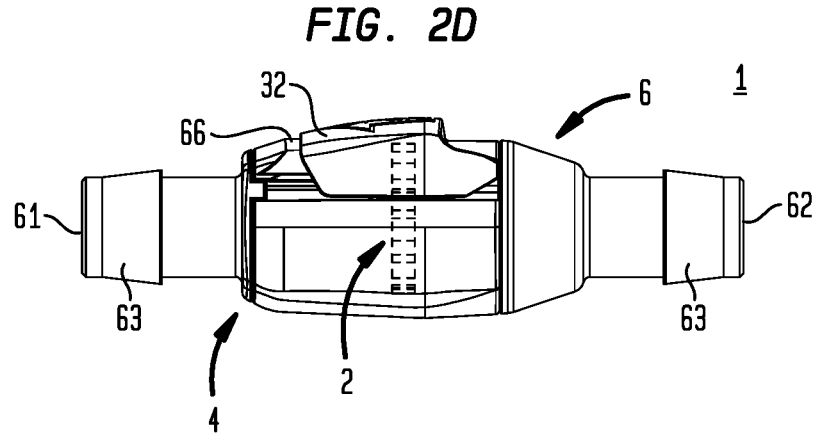
FIG. 2D is a first side view of the particular embodiment of the connector system shown in FIG. 2A.
Figure 2E:
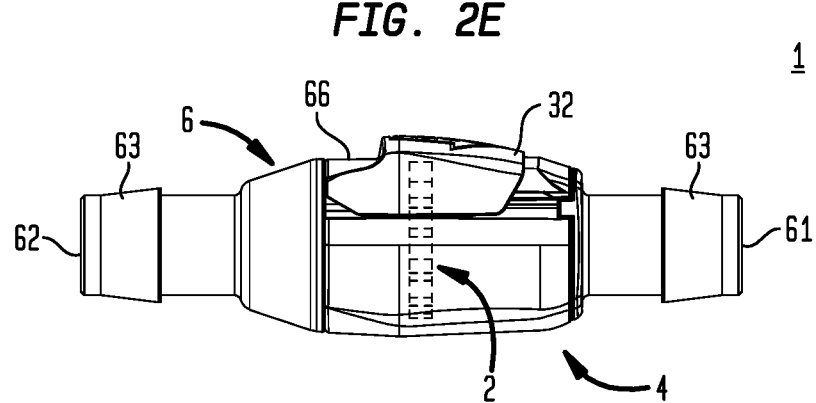
FIG. 2E is a second side view of the particular embodiment of the connector system shown in FIG. 2A.
Figure 2F:
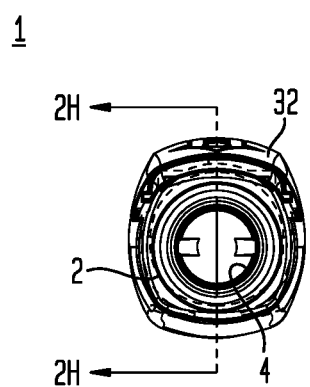
FIG. 2F is a first end view of the particular embodiment of the connector system shown in FIG. 2A.
Figure 2G:
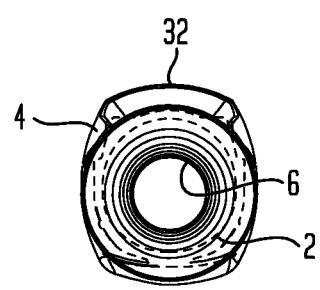
FIG. 2G is a second end view of the particular embodiment of the connector system shown in FIG. 2A.

Now referring primarily to FIG. 2A and FIG. 3A, said another way, the catch assembly (2) can be movably coupled to the female coupler (4) such that the catch (14) can move within a plane (26) which is generally orthogonal to (i) a longitudinal axis of said female coupler or (ii) the first passageway (5). For example, the catch (14) can move vertically within the plane (26); for the purposes of the present invention, the term "vertical" and derivatives thereof means positioned up and down rather than from side to side, whereby "vertical" is not intended to be limiting, particularly as to the position, orientation, or use of the invention, but instead, is intended to provide a directional reference for the depiction of the connector system (1) shown in the Figures to aid the reader's understanding of the present invention.

Following, upon matable reception of the male coupler matable end (10) within the female coupler inner space (11), the retention groove (22), the channel (21), and the catch (14) can align in the plane (26) to allow movement of the catch (14) outward from the channel (21) and upward in the plane (26) for engagement with the retention groove (22), thereby disposing the catch (14) in the engaged condition (24) to fix an axial position of the female coupler (4) in relation to the male coupler (6).

On the other hand, the catch (14) can move downwardly in the plane (26) and into the channel (21) to dispose the catch (14) in the disengaged condition (25) wherein the catch (14) is disengaged from the retention groove (22), allowing the female and male couplers (4)(6) to disconnect by axial movement away from one another.

The catch (14) can be normally biased toward the engaged condition (24) (or inwardly toward the female coupler inner space (11) or upwardly in the plane (26)) by a catch-biasing member (16), as shown in the examples of FIG. 4A through FIG. 5E. Correspondingly, the catch (14) can be normally biased toward engagement with the retention groove (22).

As but one illustrative example, the catch-biasing member (16) can be configured as a springing element (27), such as a resiliently flexible member (28) which following flexing, can return toward or to its original unflexed condition (29).

As to particular embodiments, the resiliently flexible member (28) can comprise one or more resiliently flexible arms (30) which extend outwardly (for example, radially outwardly) or downwardly (for example, radially downwardly) from the catch (14) and bear against the female coupler inner surface (12). For example, the resiliently flexible arm(s) (30) can bear against a portion of the female coupler inner surface (12) which defines the channel (21). Thus, the resiliently flexible arm(s) (30) can dispose within the channel (21) and further, can be coplanar with the catch (14) whereby both the catch (14) and the resiliently flexible arm(s) (30) move within the plane (26).

Hence, when the resiliently flexible member (28) disposes in the unflexed condition (29), which is the normal biased condition, the resiliently flexible member (28) biases the catch (14) toward the engaged condition (24) (or inwardly toward the female coupler inner space (11) or upwardly in the plane (26)).

Upon forcible urging, the resiliently flexible member (28) can be flexed toward a flexed condition (31) (as shown in the examples of FIG. 6A through FIG. 7E), which allows the catch (14) to move outwardly away from the female coupler inner space (11) or downwardly in the plane (26) to disengage from the catch-receiving element (15) and achieve a disconnected condition of the connector system (1).

As to particular embodiments, the catch-biasing member (16) can be configured as a living hinge.

As inward or upward movement of the catch (14) for engagement with the retention groove (22) can be facilitated, at least in part, by the catch-biasing member (16), movement of the catch (14) outward or downward to disengage the catch (14) from within the retention groove (22) can be facilitated, at least in part, by a release element (32) which can function as a cam (18) configured to actuate the follower (17) and correspondingly, the catch (14). The release element (32) is described in further detail in U.S. patent application Ser. Nos. 15/410,636 and 15/447,033, each of which is hereby incorporated by reference herein in its entirety.

The release element (32) can be movably coupled to the female coupler (4), whereby travel of the release element (32) along or over a female coupler outer surface (66) disengages the catch (14) from the catch-receiving element (15) to achieve the disconnected condition of the connector system (1).

For example, linear or sliding motion of the release element (32) along the female coupler outer surface (66) can be transformed into movement of the follower (17), whereby this movement of the follower (17) can forcibly urge the catch-biasing member (16) away from the normal unflexed condition (29) and toward the flexed condition (31) to allow the catch (14) to move outwardly away from the female coupler inner space (11) or downwardly in the plane (26) to disengage from the retention groove (22).

Figure 9A:
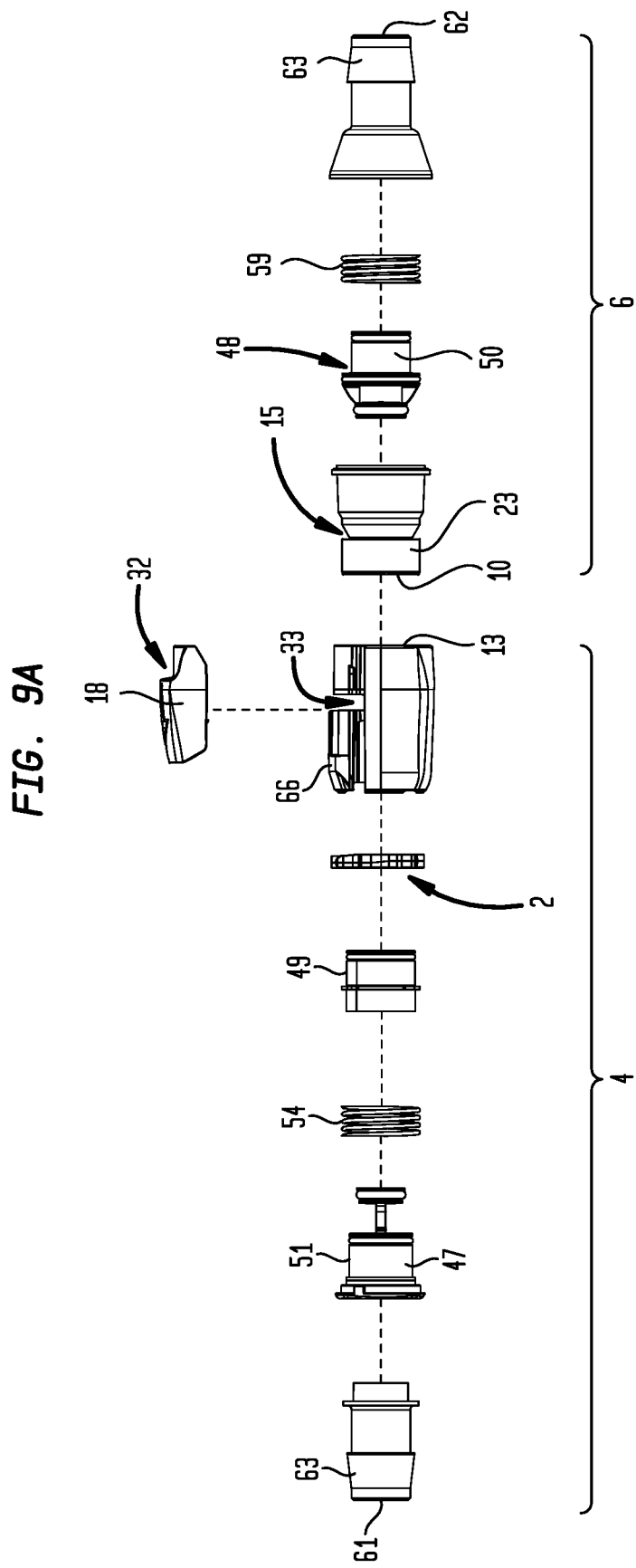
FIG. 9A is an exploded first side view of a particular embodiment of the connector system.
Figure 9B:
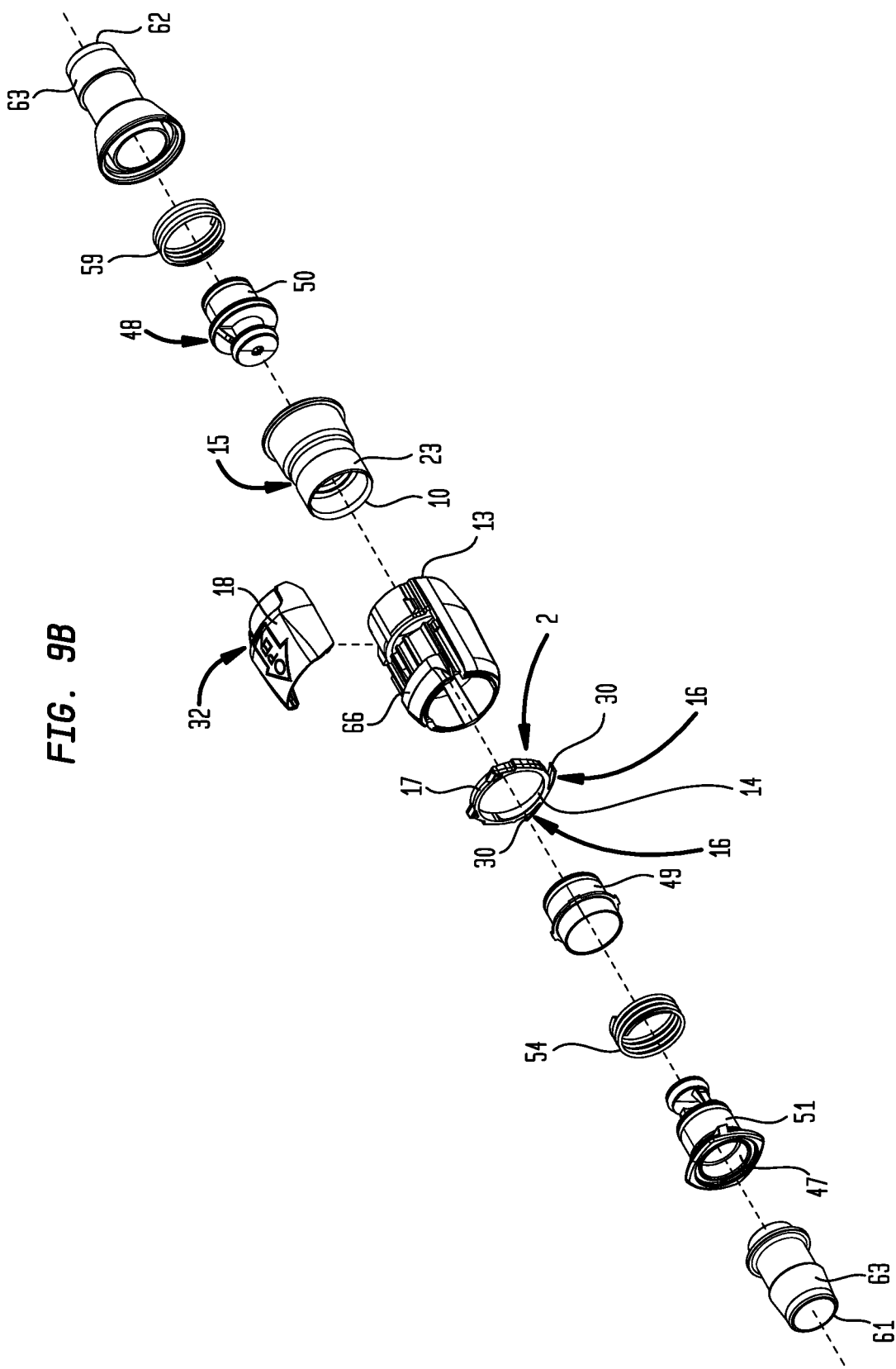
FIG. 9B is a perspective view of the particular embodiment of the connector system shown in FIG. 9A.
Figure 9C:
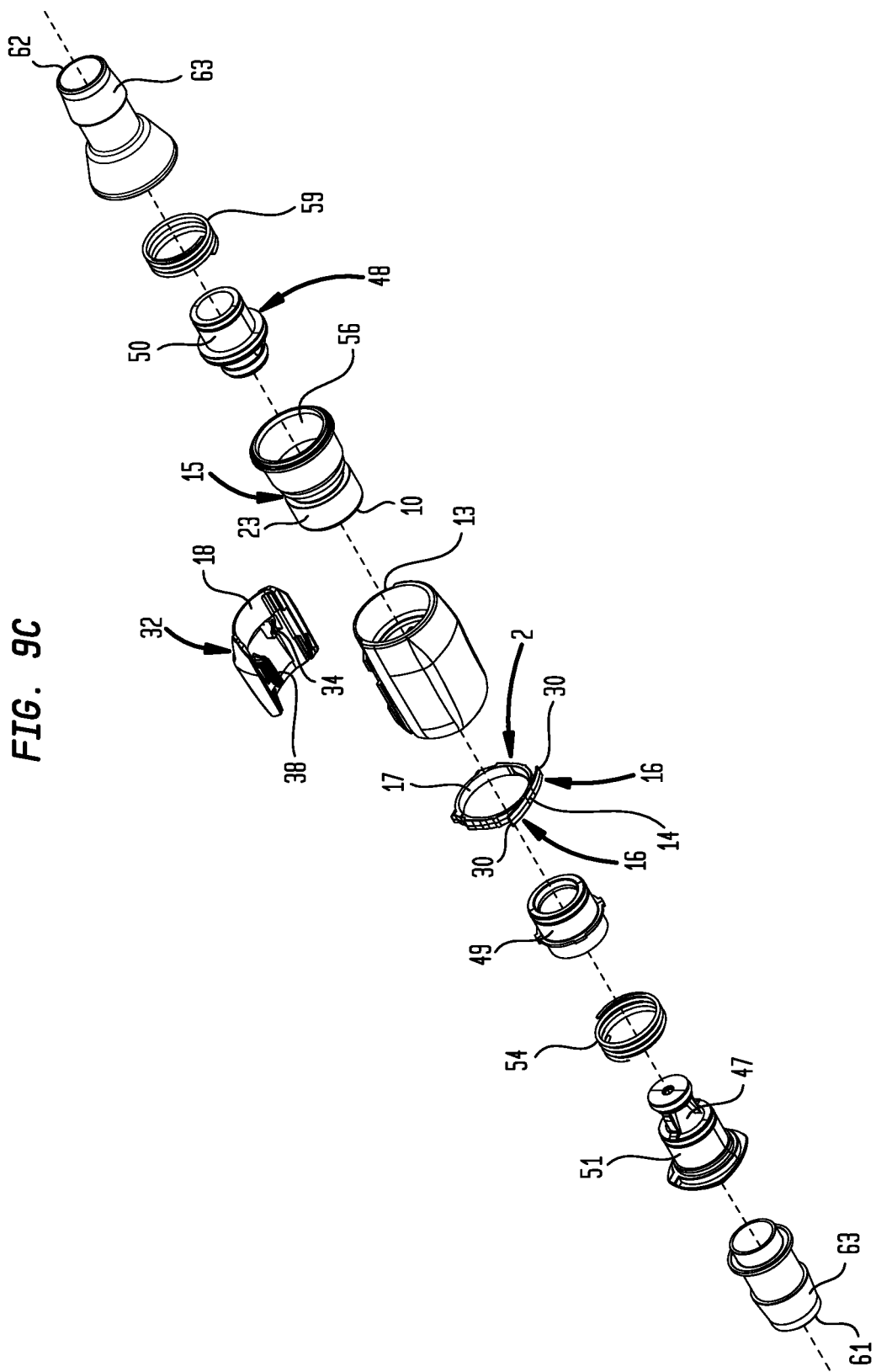
FIG. 9C is a perspective view of the particular embodiment of the connector system shown in FIG. 9A.

Thus, the follower (17) can be operably coupled to the catch-biasing member (16) and correspondingly, the catch (14). Additionally, the follower (17) can be movably coupled to the female coupler (4) proximate the female coupler outer surface (66). For example, the follower (17) can be movably disposed within an opening (33) defined by the female coupler outer surface (66) (as shown in the example of FIG. 9A), whereby the opening (33) can be sufficiently configured to allow movement of the follower (17) through the opening (33) and inward toward the female coupler inner space (11) or downward in the plane (26), or outward away from the female coupler inner space (11) or upward in the plane (26). Further, the follower (17) can be movably coupled to the female coupler (4) beneath the release element (32).

Now referring primarily to FIG. 4B, FIG. 5E, FIG. 6B, and FIG. 7E, a release element inner surface (34), which disposes proximate (or adjacent) the female coupler outer surface (66), can provide a cam surface (35) having a locking surface (36) and an unlocking surface (37), both of which can separately interact with or directly contact the follower (17) to result in movement of the catch (14).

The unlocking surface (37) extends downwardly toward the female coupler outer surface (66) a greater distance than the locking surface (36), thereby disposing the unlocking surface (37) closer to the female coupler outer surface (66) than the locking surface (36). Said another way, the locking surface (36) extends upwardly away from the female coupler outer surface (66) a greater distance than the unlocking surface (37), thereby disposing the locking surface (36) farther from the female coupler outer surface (66) than the unlocking surface (37).

Correspondingly, movement of the cam surface (35) over the follower (17) to align (or contact) the locking surface (36) with the follower (17) allows the catch (14) to be biased inwardly or upwardly by the catch-biasing member (16) toward engagement with the retention groove (22) to achieve the connected condition of the connector system (1). Conversely, movement of the cam surface (35) over the follower (17) to align (or contact) the unlocking surface (37) with the follower (17) biases the catch-biasing member (16) toward the flexed condition (31), accordingly biasing the catch (14) outwardly or downwardly and away from the retention groove (22), thereby permitting the catch (14) to disengage from the retention groove (22) to achieve the disengaged condition (25).

Now referring primarily to FIG. 2H, FIG. 3H, and FIG. 4A through FIG. 5E, a release element-biasing member (38), for example a resiliently compressible member (39), can bias the release element (32) toward a release element first position (40) when in a non-compressed condition (41), which is the normal biased condition. When in the release element first position (40), the locking surface (36) aligns with (or contacts) the follower (17) and correspondingly biases the catch (14) inwardly or upwardly and toward engagement with the retention groove (22) to achieve the connected condition of the connector system (1).

Now referring primarily to FIG. 6A through FIG. 7E, upon forcible urging, the resiliently compressible member (39) can be compressed toward a compressed condition (42), disposing the release element (32) in a release element second position (43) in which the unlocking surface (37) aligns with (or contacts) the follower (17), biasing the catch-biasing member (16) toward the flexed condition (31), allowing the catch (17) to move outwardly away from the retention groove (22) to achieve the disconnected condition of the connector system (1).

As to particular embodiments, the catch (14), the catch-biasing member (16), and the follower (17) can be integrated to provide a catch-assembly (2) which (i) can be a one-piece construct or (ii) can be formed as a one-piece construct. Said another way, the catch (14), the catch-biasing member (16), and the follower (17) can be integrally formed, meaning connected together so as to make up a single complete piece or unit, or so as to work together as a single complete piece or unit, and so as to be incapable of being easily dismantled without destroying the integrity of the piece or unit.

As to particular embodiments, the catch assembly (2) can comprise an annular member (44), whereby a first portion (45) of the annular member (44) can provide the catch (14) and an opposing second portion (46) of the annular member (44) can provide the follower (17). As to this particular embodiment, the catch-biasing member (16) can extend outwardly from the first portion (45) of the annular member (44) which provides the catch (14).

As to particular embodiments, the annular member (44) can be movably coupled to the female coupler (4) such that the catch (14) can move inwardly toward or into the female coupler inner space (11) as illustrated by the first arrow (19) shown in FIG. 4B, or the catch (14) can move outwardly away from or out of the female coupler inner space (11) as illustrated by the second arrow (20) shown in FIG. 6B.

Further, the annular member (44) can be movably coupled to the female coupler inner surface (12) which defines the female coupler inner space (11). As but one illustrative example, the annular member (44) can be movably disposed within the channel (21) inset within the female coupler inner surface (12).

Thus, upon matable reception of the male coupler matable end (10) within the female coupler inner space (11), the male coupler matable end (10) can pass through an annular member opening defined by the annular member (44) to achieve the connected condition of the connector system (1); correspondingly, the fluid flow path (9) can pass through the annular member opening.

First Valve

As to particular embodiments, the connector system (1) can further include at least one conduit (47)(48) and at least one valve (49)(50) operable to interrupt fluid flow through the conduit (47)(48).

Figure 2H:
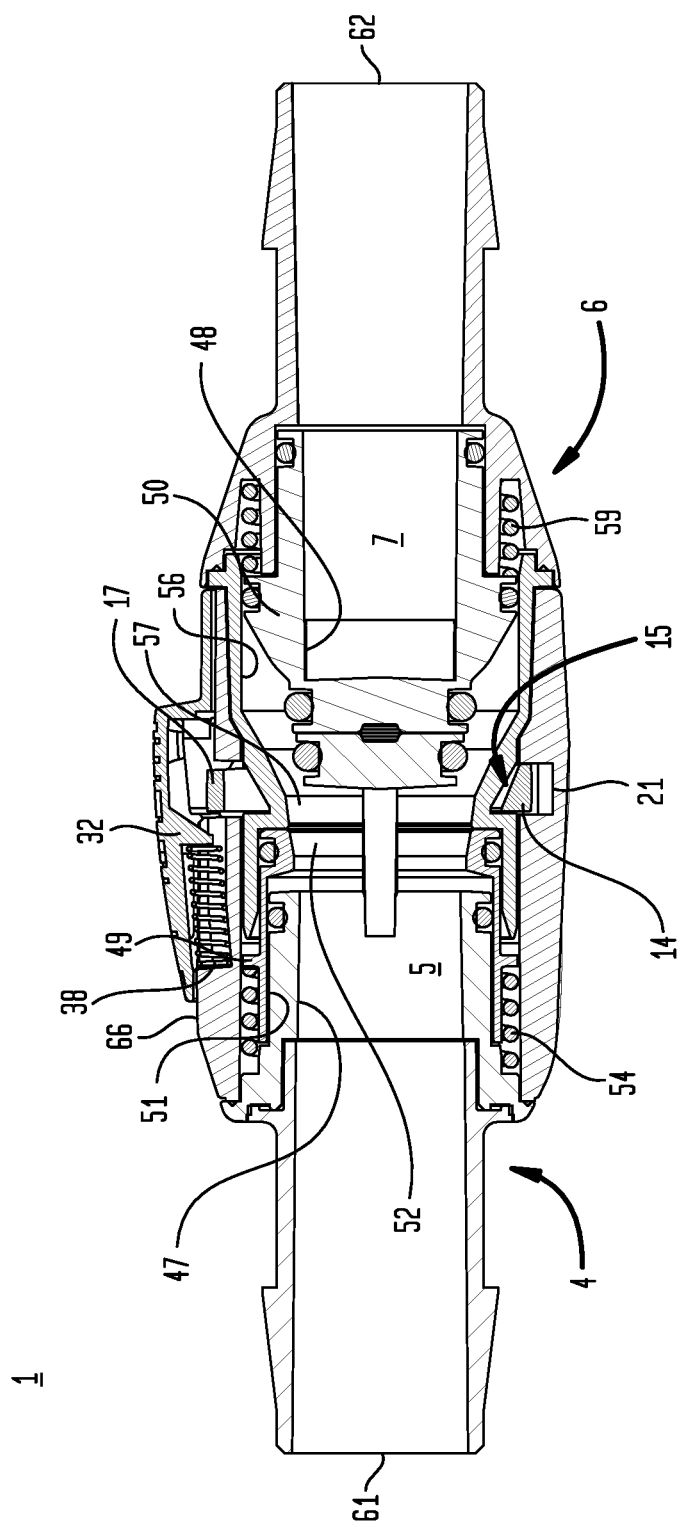
FIG. 2H is a cross-sectional view of the particular embodiment of the connector system shown in FIG. 2F.

Now referring primarily to FIG. 2H and FIG. 3H, the female coupler (4) can include a first conduit (47) defining a first passageway (5) (which as to particular embodiments, may include a fixed or removable filter) and a first valve (49) operable to interrupt fluid flow through the first passageway (5). The first valve (49) can be movable within a first valve seat (51) to sealably occlude a first port (52) in fluid communication with the first passageway (5), thereby providing a first passageway closed condition (53) in which fluid flow through the first port (52) and accordingly, through the first passageway (5), is interrupted.

The first valve (49) can be biased by a first valve-biasing member (54) which biases the first valve (49) toward a first valve closed position (55) in which the first valve (49) sealably occludes the first port (52), for example by sealably overlaying the first port (52), to provide the first passageway closed condition (53).

The first valve (49) and the first valve-biasing member (54) are described in further detail in U.S. patent application Ser. Nos. 15/410,636 and 15/447,033, each of which is hereby incorporated by reference herein in its entirety.

Second Valve

Again referring primarily to FIG. 2H and FIG. 3H, the male coupler (6) can include a second conduit (48) defining a second passageway (7) (which as to particular embodiments, may include a fixed or removable filter) and a second valve (50) operable to interrupt fluid flow through the second passageway (7).

The second valve (50) can be movable within a second valve seat (56) to sealably occlude a second port (57) in fluid communication with the second passageway (7), thereby providing a second passageway closed condition (58) in which fluid flow through the second port (57) and accordingly, through the second passageway (7), is interrupted.

The second valve (50) can be biased by a second valve-biasing member (59) which biases the second valve (50) toward a second valve closed position (60) in which the second valve (50) sealably occludes the second port (57), for example by sealably overlaying the second port (57), to provide the second passageway closed condition (58).

The second valve (50) and the second valve-biasing member (59) are described in further detail in U.S. patent application Ser. Nos. 15/410,636 and 15/447,033, each of which is hereby incorporated by reference herein in its entirety.

Tubing

Now referring primarily to FIG. 1, as to particular embodiments, the connector system (1), as described above, can further include at least one tube (3) coupled to a connector system end (61)(62), which can be configured as a barb (63). Accordingly, the tube (3) can engage with the barb (63), for example via frictional engagement about the barb (63), to securely couple the tube (3) to the connector system (1). As to particular embodiments, a first tube (64) can be coupled to connector system first end (61) and a second tube (65) can be coupled to the connector system second end (62), wherein the connector system (1) functions to fluidicly connect the first and second tubes (64)(65).

As to other particular embodiments, the connector system first and/or second ends (61)(62) can be configured as a luer lock fitting, a threaded fitting which can be threaded externally or internally, or any conventional or non-conventional end fitting which may be useful for coupling a tube (3) to a connector system end (61)(62).

As to other particular embodiments, the connector system first and/or second ends (61)(62) can be configured as a flange which may be useful for coupling a tube (3) to a connector system end (61)(62).

A method of making a particular embodiment of a connector system (1) for releasably connecting tubes (3) can include providing a female coupler (4) having a first passageway (5); providing a male coupler (6) having a second passageway (7); and providing a catch assembly (2) including a catch (14) movably coupled to the female coupler (4), a catch-biasing member (16) which biases the catch (14), and a follower (17) responsive to a cam (18); whereby the catch (14) is responsive to the follower (17) and correspondingly, the cam (18).

The method of making the connector system (1) can further include providing additional components of the connector system (1) as described above and in the claims.

Components of the connector system (1) can be formed from one or more of any of a numerous and wide variety of materials capable of providing a functional connector system (1). By way of illustrative example, the material can include or consist of: rubber, rubber-like material, plastic, plastic-like material, acrylic, polyamide, polyester, polypropylene, polyethylene, polyvinyl chloride-based materials, silicone-based materials, or the like, or combinations thereof. Additional illustrative examples can include polymeric materials or resins, for example thermoplastics, such as acrylic, nylon, polybenzimidazole, polyethylene, polypropylene, polystyrene, polyvinyl chloride, polytetrafluoroethylene, or the like, or combinations thereof; thermosets, such as polyester fiberglass, polyurethanes, rubber, polyoxybenzylmethylenglycolanhydride, urea-formaldehyde foam, melamine resin, epoxy resin, polyimides, cynate esters, polycyanurates, polyester resin, or the like, or combinations thereof; elastomers, such as natural polyisoprene, synthetic polyisoprene, polybutadiene, chloropene rubber, butyl rubber, styrene-butadiene rubber, nitrile rubber, ethylene propylene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermal plastic elastomer (TPE), or the like, or combinations thereof.

As to particular embodiments, one or more components of the connector system (1) can be formed from an antibacterial material(s).

As to particular embodiments, one or more components of the connector system (1) can be formed entirety from non-metallic material(s).

Additionally, components of the connector system (1) can be produced from any of a wide variety of processes depending upon the application, such as press molding, injection molding, fabrication, machining, printing, additive printing, or the like, or combinations thereof, as one piece or assembled from a plurality of pieces into a component of the connector system (1).

As to particular embodiments, one or more components of the connector system (1) can be disposable or reusable, depending upon the application.

A method of using a particular embodiment of a connector system (1) for releasably connecting tubes (3) can include obtaining the connector system (1) as above described, coupling a first tube (64) to the female coupler (4); coupling a second tube (65) to the male coupler (6); and releasably coupling the female and male couplers (4)(6) to achieve the connected condition of the connector system (1).

As to particular embodiments, the method can further include flowing fluid through the fluid flow path (9).

As to particular embodiments, the method can further include forcibly urging the release element (32) to travel along the female coupler outer surface (66) to disengage the catch (14) from the catch-receiving element (15) to achieve the disconnected condition of the connector system (1).

As can be easily understood from the foregoing, the basic concepts of the present invention may be embodied in a variety of ways. The invention involves numerous and varied embodiments of a connector system and methods for making and using such a connector system, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "connector" should be understood to encompass disclosure of the act of "connecting"—whether explicitly discussed or not—and, conversely, were there effectively disclosure of the act of "connecting", such a disclosure should be understood to encompass disclosure of a "connector" and even a "means for connecting". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Thus, the applicant(s) should be understood to claim at least: i) each of the connector systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A connector system for releasably connecting tubes, comprising:
a female coupler; and
a catch assembly comprising:
a catch movably coupled to said female coupler;
a catch-biasing member comprising a pair of resiliently flexible arms which outwardly extend from said catch; and
a follower responsive to a cam;
said catch responsive to said follower and correspondingly, said cam; and
said catch assembly comprising a one-piece construct.

2. The connector system of claim 1, wherein said catch, said catch-biasing member, and said follower are formed as said one-piece construct.

3. The connector system of claim 1, wherein catch assembly comprises an annular member.

4. The connector system of claim 3, wherein said annular member comprises a first portion which provides said catch and an opposing second portion which provides said follower.

5. The connector system of claim 4, wherein said catch-biasing member outwardly extends from said first portion of said annular member which provides said catch.

6. The connector system of claim 1, wherein said catch assembly comprises a monolithic construct.

7. The connector system of claim 1, said pair of resiliently flexible aims outwardly extending from said catch in opposing directions.

8. The connector system of claim 1, said catch-biasing member disposed opposite said follower.

9. The connector system of claim 1, further comprising:
a male coupler; and
a catch-receiving element coupled to said male coupler;
wherein upon releasable matable axial coupling of said female and male couplers, said catch engages with said catch-receiving element to fix an axial position of said female coupler in relation to said male coupler.

10. A connector system for releasably connecting tubes, comprising:
a female coupler; and
a catch assembly comprising:
a catch movably coupled to said female coupler;
a catch-biasing member comprising a pair of resiliently flexible arms which outwardly extend from said catch; and
a follower responsive to a cam;
said catch responsive to said follower and correspondingly, said cam; and
said catch movably coupled to said female coupler such that said catch is capable of:
inward movement toward a female coupler inner space defined by a female coupler inner surface of said female coupler; and
outward movement away from said female coupler inner space.

11. The connector system of claim 10, wherein said catch is movably coupled to said female coupler inner surface.

12. The connector system of claim 11, wherein said catch is movably disposed within a channel inset within said female coupler inner surface; and
wherein said channel communicates with said female couple inner space.

13. The connector system of claim 12, further comprising:
a male coupler; and
a catch-receiving element coupled to said male coupler;
wherein upon releasable matable axial coupling of said female and male couplers, said catch engages with said catch-receiving element to fix an axial position of said female coupler in relation to said male coupler.

14. The connector system of claim 13, wherein said catch-receiving element comprises a retention groove disposed within a male coupler outer surface proximate said male coupler matable end.

15. The connector system of claim 14, wherein upon releasable matable axial coupling of said female and male couplers, said retention groove aligns with said channel to allow said catch to move outwardly from said channel and inwardly toward said female coupler inner space for engagement with said retention groove to dispose said catch in an engaged condition to fix said axial position of said female coupler in relation to said male coupler.

16. The connector system of claim 15, wherein said catch is movably coupled to said female coupler such that said catch is capable of movement within in a plane which is generally orthogonal to a longitudinal axis of said female coupler.

17. The connector system of claim 16, wherein upon releasable matable axial coupling of said female and male couplers, said retention groove, said channel, and said catch align in said plane to allow said catch to move outwardly from said channel and upwardly in said plane for engagement with said retention groove to dispose said catch in said engaged condition to fix said axial position of said female coupler in relation to said male coupler.

18. The connector system of claim 17, wherein said catch-biasing member normally biases said catch inwardly toward said female coupler inner space or upwardly in said plane.

19. A connector system for releasably connecting tubes, comprising:
a female coupler; and
a catch assembly comprising:
a catch movably coupled to said female coupler;
a catch-biasing member comprising a pair of resiliently flexible arms which outwardly extend from said catch; and
a follower responsive to a cam;
said catch responsive to said follower and correspondingly, said cam; and
said cam provided by a release element which is movably coupled to said female coupler.

20. The connector system of claim 19, further comprising:
a male coupler; and
a catch-receiving element coupled to said male coupler;
wherein upon releasable matable axial coupling of said female and male couplers, said catch engages with said catch-receiving element to fix an axial position of said female coupler in relation to said male coupler.

* * * * *